(12) United States Patent
Van Eck-Smit et al.

(10) Patent No.: US 8,524,194 B2
(45) Date of Patent: Sep. 3, 2013

(54) RADIOLABELLED MMP SELECTIVE COMPOUNDS

(75) Inventors: Bertha Louise Frederike Van Eck-Smit, Leusden (NL); Victorine Augustine Pinas, Amsterdam (NL); Albert Dirk Windhorst, Alphen Aan Den Rijn (NL)

(73) Assignee: Academisch Medisch Centrum Bij de Universiteit van Amsterdam, Amsterdam (NL)

( * ) Notice: Subject to any disclaimer, the term of this patent is extended or adjusted under 35 U.S.C. 154(b) by 242 days.

(21) Appl. No.: 12/992,592

(22) PCT Filed: May 14, 2009

(86) PCT No.: PCT/NL2009/050262
§ 371 (c)(1),
(2), (4) Date: Mar. 14, 2011

(87) PCT Pub. No.: WO2009/139634
PCT Pub. Date: Nov. 19, 2009

(65) Prior Publication Data
US 2011/0171133 A1    Jul. 14, 2011

Related U.S. Application Data

(60) Provisional application No. 61/127,663, filed on May 14, 2008, provisional application No. 61/127,946, filed on May 15, 2008.

(30) Foreign Application Priority Data

May 14, 2008    (EP) ..................... 08156176

(51) Int. Cl.
*A61K 49/04* (2006.01)
(52) U.S. Cl.
USPC ............. 424/9.2; 562/427; 562/430; 562/448
(58) Field of Classification Search
USPC ................. 424/9.1, 9.2, 9.4; 562/427, 430, 562/448, 621
See application file for complete search history.

(56) References Cited

U.S. PATENT DOCUMENTS 6,156,798 A * 12/2000 Reiter .......................... 514/562

FOREIGN PATENT DOCUMENTS

| EP | 1 466 899 | 10/2004 |
|---|---|---|
| WO | WO-2005/049005 | 6/2005 |

OTHER PUBLICATIONS

International Search Report for PCT/NL2009/050262, mailed on Aug. 25, 2009, 2 pages.
International Preliminary Report on Patentability for PCT/NL2009/050262, issued Nov. 17, 2010, 6 pages.
Kuhnast et al., Journal of Labelled Compounds and Radiopharmaceuticals (2003) 46(6):539-553.

* cited by examiner

*Primary Examiner* — Michael G Hartley
*Assistant Examiner* — Jagadishwar Samala
(74) *Attorney, Agent, or Firm* — Morrison & Foerster LLP

(57) ABSTRACT

The invention is directed to radiolabelled MMP selective compounds, a processes for the preparation thereof, and uses thereof. The derivatives of the invention have formula (I) wherein Y represents O, $CH_2$, $(CH_2)_2$, S, NH, or $C(=O)NH$; X represents 1-5 substituents, wherein said substituents can be the same or different and wherein at least one of said substituents comprises a radioisotope suitable for PET and/or SPECT and/or a β-emitter; Z is S; Q is chosen from the group consisting of 3-pyridyl and carboxyl; and R is chosen from the group consisting of $C(=O)$—NH—OH, (II), (III), (IV). The MMP selective compounds of the invention are selective for MMPs and can be used for the identification and treatment of unstable atherosclerotic plaques.

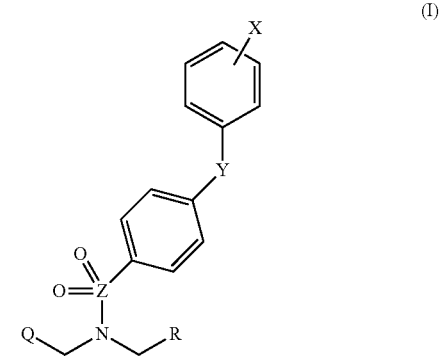

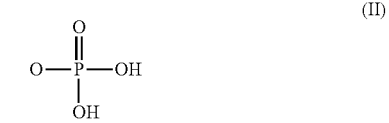

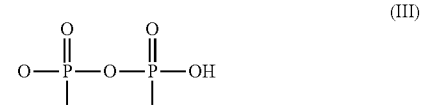

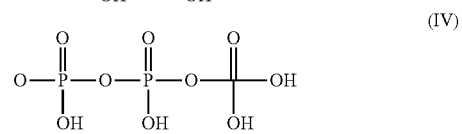

17 Claims, 2 Drawing Sheets

Figure 3:
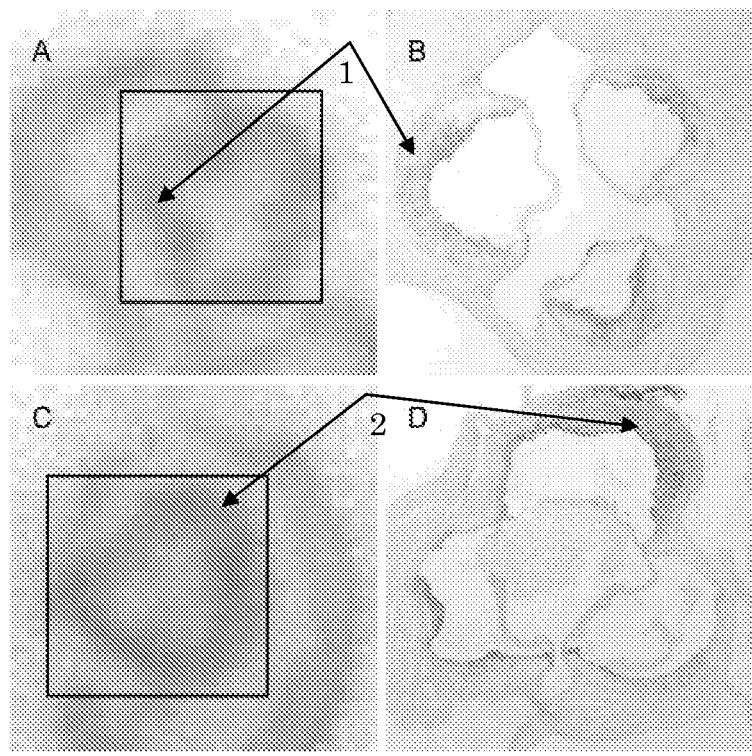

Figure 3. Phosphor-imager (A, C) and Oil-red-O (B, D) staining of aortic valves area.

RADIOLABELLED MMP SELECTIVE COMPOUNDS

CROSS-REFERENCE TO RELATED APPLICATIONS

This application is the national phase of PCT application PCT/NL2009/050262 having an international filing date of 14 May 2009, which claims benefit of European application No. 08156176.3, filed 14 May 2008, and which claims priority under 35 U.S.C. §119(e) to U.S. provisional application Nos. 61/127,663, filed 14 May 2008, and 61/127,946, filed 15 May 2008. The contents of the above patent applications are incorporated by reference herein in their entirety.

The invention is directed to radiolabelled MMP selective compounds, processes for the preparation thereof, methods for labelling MMP, a complex of said MMP selective compounds and MMP, uses of said compounds, a method for providing a MMP or a MMP expressing cell with a label, a method for quantifying MMP on a MMP expressing cell, a method for identifying unstable coronary plaques, a method for in vivo identification of the effectiveness of a potential medicine against unstable plaques, and a method for treating a coronary atherosclerotic disease.

The radiolabelled MMP selective compounds of the invention can be used as diagnostic imaging agents for in vivo imaging of vulnerable plaques. The imaging agents are derivatives of highly potent and selective inhibitors of matrix metalloproteinases (MMPs), enzymes which are released in unstable plaques. Since numerous pathogenic conditions are characterised by elevated levels of specific MMPs, the inhibitors described in the invention may also be employed for diagnosis and therapy monitoring of various other diseases.

Cardiovascular disease due to atherosclerosis is the major cause of mortality and morbidity in the Western world. In the United States, nearly 50% of all deaths are generally attributed to diseases that are associated with atherosclerosis, namely coronary artery disease and strokes. Atherosclerosis may start early in life, but over many years, atherosclerotic lesions are clinically silent. When symptoms occur, they already indicate an advanced state of the disease, rendering therapeutic intervention more difficult. In fact, early stages of atherosclerosis are a normal healing response to injury, but distortion of the delicate balance of processes involved in healing may entail the formation of atheromatous plaques, which may result from accumulation of cellular and extracellular substances, such as activated smooth muscle cells (VSMCs), macrophages, lymphocytes, connective tissue and lipid build-up in the vessel wall. Atheromatous plaques may further increase in size until they form mature plaques, which may compromise blood flow to critical organs such as heart, brain and kidney, finally causing their ischemic compromise. Although atheroscerotic plaques may be classified into numerous types depending on their morphology and composition, the most important distinction is between two major types: stable and unstable (vulnerable) plaques (Ranganna et al., 2006; Vallabhajosula et al., 1997). Acute clinical events most frequently arise from disruption of lipid-rich vulnerable plaques. Given the high occurrence of atherosclerosis, the significantly improved prognosis associated with early therapeutic intervention, and the need for effective monitoring during therapy, development of diagnostic tools for the detection of unstable plaques is expected to become a key area in academic and industrial research worldwide.

A major limitation of most conventional imaging techniques such as angiography, angioscopy, intravascular ultrasound, and electron beam CT, is their inability to discriminate between stable and unstable plaques. In contrast, radiotracers that selectively bind to molecular targets exclusively or predominantly localised in unstable plaques, allow specific imaging of these plaques using the non-invasive techniques Positron Emission Tomography (PET) and Single Photon Emission Computed Tomography (SPECT) (Davies et al., 2006). At present, the number of radionuclide tracers under investigation for nuclear imaging of vulnerable plaques is limited (Choi et al., 2007; Davies et al., 2006). The majority of tracers comprises radiolabelled derivatives of proteins involved in macrophage recruitment (monocyte chemotactic protein-1), foam cell formation (oxidised low density lipoprotein, oxLDL), and macrophage apoptosis (annexin-A5). Concerning low molecular weight chemical radiotracers, only the glucose analogue $^{18}$F-fluorodeoxyglucose ($^{18}$F-FDG) involved in macrophage activity, and small-molecule inhibitors of matrix metalloproteinases (MMPs) have been studied for the PET-imaging of vulnerable plaques. $^{18}$F-FDG accumulation in atherosclerotic plaques has first been noted in patients undergoing PET imaging for diverse unrelated indications (Yun et al., 2001), but it was soon thereafter established that FDG-PET is capable to selectively image the enhanced metabolic activity associated with inflammation in vulnerable plaques (Davies et al., 2005; Rudd et al., 2002; Tawakol et al., 2006). Recent studies indicate that FDG-PET may be employed to monitor reduction of plaque inflammation during therapy both in animals (Ogawa et al., 2006) and humans (Tahara et al., 2006). Despite these promising results, a major concern associated with $^{18}$F-FDG is its comparably low specificity, since this glucose analogue is principally taken up by all cells in proportion to their metabolic activity. Consequently, imaging plaques in metabolically active tissues such as the heart and brain remains problematic (Rudd et al., 2002). Therefore, developments of PET ligands with high specificity for targets exclusively found in vulnerable plaques are urgently needed.

Matrix metalloproteinases, which are responsible for the transition of stable to unstable plaques by catalysing the breakdown of the connective tissue of the fibrous cap, are expected to be excellent targets for selective imaging of unstable plaques (Davies et al., 2006). Although numerous small-molecule matrix metalloproteinase inhibitors (MMPIs) have been developed in the past decades initially owing to their potential application in cancer chemotherapy but more recently also for therapy of inflammatory and vascular diseases (Hu et al., 2007; Rouis, 2005; Skiles et al., 2004), development of radiolabelled MMPs for diagnostic purposes is only at its beginning (Wagner et al., 2006). Recent studies have demonstrated successful SPECT imaging of MMP activity in MMP-rich atherosclerotic lesions of ApoE$^{-/-}$ mice using the $^{123}$I-labelled analogue of the broad spectrum MMP inhibitor CGS27023A (Schäfers et al., 2004). One of the major limitations of this and other radiolabelled broad-spectrum MMP inhibitors prepared by the same group (Wagner et al., 2007) is their low selectivity for specific MMP subtypes, which apart from the reduced image quality related to undesired background activity originating from the presence of MMP subclasses in various other tissues, also leads to enhanced toxicity of these broad-spectrum MMP inhibitors. The severe side effects encountered with broad-spectrum MMPIs developed in the past have mainly been associated with inhibition of the MMP1 collagenase (Skiles et al., 2001). Fortunately, MMP subtypes other than MMP1, namely MMP2 and MMP9, are playing a major role in the development of unstable plaques offering the perspective to design highly specific radiolabelled MMP inhibitors.

Kuhnast et al. described the synthesis and labelling of (2R)-3-methyl-2-[[4-[(4-methoxybenzoyl)amino]benzenesulphonyl]amino]butanoic acid, a MMP-2 and MMP-9 inhibitor.

The inventors have now found new radiolabelled MMP selective compounds based on recently described highly potent and subtype selective inhibitors of MMPs (Santos et al., 2006).

Accordingly, in a first aspect the invention is directed to compounds having the general formula (I),

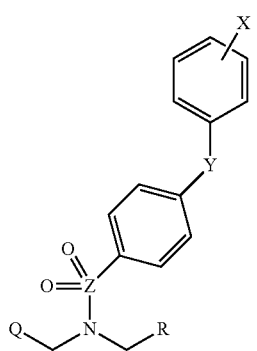

(I)

wherein
Y represents O, CH$_2$, (CH$_2$)$_2$, S, NH, or C(=O)NH;
X represents 1-5 substituents,
  wherein said substituents can be the same or different and wherein at least one of said substituents comprises a radioisotope suitable for PET and/or SPECT and/or a β-emitter;
Z is S;
Q is chosen from the group consisting of 3-pyridyl and carboxyl; and
R is chosen from the group consisting of C(=O)—NH—OH,

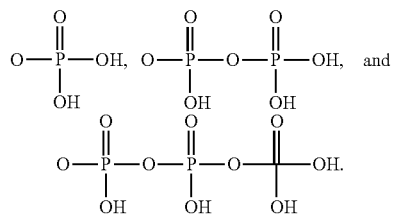

X can comprise one or more radioisotopes selected from the group consisting of $^{123}$I, $^{124}$I, $^{125}$I, $^{131}$I, $^{76}$Br, $^{18}$F, and $^{11}$C.

In an embodiment, X can comprise a saturated or unsaturated alkyl chain incorporating $^{123}$I, $^{124}$I, $^{125}$I, $^{76}$Br, $^{18}$F, O$^{11}$CH$_3$, and other radioisotopes suitable for PET or SPECT. In an embodiment X represents a single substituent, which can be either in ortho, meta, or para position.

One or more of the substituents of X can comprise a saturated or unsaturated C$_{1-10}$ alkyl chain. Further, one or more of the substituents of X can comprise one or more selected from halogens, aldehydes, ketones, carboxylates, nitriles, azides, nitro-groups, nitroso-groups, esters, optionally substituted saturated or unsaturated linear or branched alkyl chains, aryls, heteroaryls, saturated or unsaturated linear or branched alkoxys, aryloxys, saturated or unsaturated alkylaminos, and arylaminos. Preferably, one or more of the substituents of X is selected from the group consisting of saturated or unsaturated linear or branched alkoxys comprising a halogen or radioisotope thereof, aryloxys comprising a halogen or radioisotope thereof, saturated or unsaturated alkylaminos comprising a halogen or radioisotope thereof, and arylaminos comprising a halogen or radioisotope thereof. Preferably, X is a single radiolabelled substituent in the para position with respect to Y.

In a specific embodiment X comprises a β-emitter. $^{131}$I can be used as a suitable radioisotope to emit β-radiation. The emitted β-radiation may be advantageously used in order to locally destroy tumour cells, since it is well-known that tumour cells have an elevated concentration of MMPs.

Preferably, Y is an oxygen atom. In a preferred embodiment, both Y is O and X is a single radiolabelled substituent in the para position with respect to Y.

In a particularly preferred embodiment R equals C(=O)—NH—OH. It was found that these hydroxamate compounds can bind in the MMP pocket with high specificity. Very promising results have been obtained with compounds of formula (I), wherein Z is S, Q is carboxyl, and R is C(=O)—NH—OH.

In a further aspect the invention is directed to processes for preparing the radiolabelled MMP selective compounds according to formula (I), to intermediates thereof, and to a process for preparing the intermediates.

Initial attempts to synthesise the non-radioactive analogues of the compounds according to formula (I) starting from iminodiacetic acid (IDA) in analogy to the procedure described by Santos et al. afforded unacceptably low yields. Therefore, the inventors now came up with an alternative highly efficient synthetic strategy, which gives rise to much higher yield.

Thus, in a further aspect, the invention is directed to a process for preparing an intermediate compound for the radiolabelled MMP selective compounds described above, comprising reacting di-protected iminodiacetic acid with arylsulphonyl or arylphosphonyl halides of formula (II)

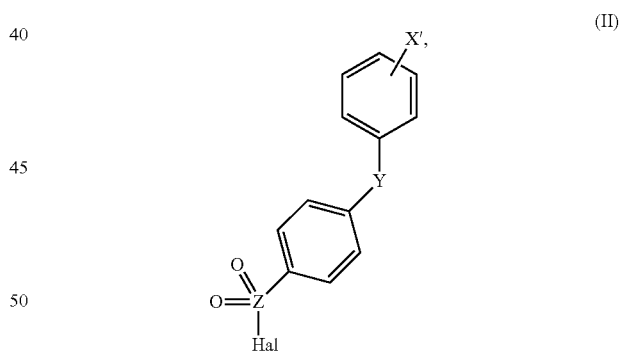

(II)

wherein
Y represents O, CH$_2$, (CH$_2$)$_2$, S, or NH;
X' represents 1-5 substituents,
  wherein said substituents can be the same or different, and wherein
    one or more of said substituents comprises a halogen, or
    at least one of said substituents is a leaving group and at least another one of said substituents is an activating group,
Z is S; and
Hal is a halogen,
in the presence of an equimolar amount of a suitable base, such as triethylamine, DIPEA, pyrrolidine, piperidine, piperazine, morpholine, N-methyl-morpholine, pyridine, imidazole, imidazoline, or imidazolidine. This is not a limitative list. Suitable bases for this reaction are well-known to the person skilled in the art who will be able to find other suitable alternatives. After radiolabelling, deprotection followed by condensation can give rise to the final radiolabelled hydroxamate derivative.

The substituents X' can comprise a halogen. Preferably, one or more of the substituents X' is or are a halogen. In a preferred embodiment X' comprises iodine or bromine. This halogen in the one or more X' substituents can be used for the preparation of precursors for trialkylstannyl (Wester, 2003; Cai et al. 2008; Schubiger et al. 2006) and trialkylsilyl compounds.

It is also possible that X' comprises a combination of an activating group with a leaving group. The leaving group is preferably chosen from the group consisting of $NO_2$, $[N(alkyl)_3]^+$, OTosyl, $N_3$, F, Br, and I. The activating group is preferably chosen from the group consisting of CHO, $NO_2$, $SO_2CH_3$, $[N(alkyl)_3]^+$, $CF_3$, CN, CO-alkyl, CO-aryl, COOH, Br, Cl, and I. In the case of $[N(alkyl)_3]^+$, the dialkylamine compound $(N(alkyl)_2)$ is e.g. reacted with methyl iodided ($CH_3I$) or methyl triflate ($H_3C$—O—$SO_2$—$CF_3$) to yield the corresponding trialkylamine salts, i.e. $[N(alkyl)_3]^+Cl^-$ or $CF_3SO_3^-$.

Preferably, the iminodiacetic acid is protected as its di-tert-butyl ester. The halogen Hal can be any halogen, such as chlorine, bromine, iodine, and fluorine. Good results have been achieved with chlorine. The intermediate N-aryl iminodiacetic acid diesters (I) are highly stable and can be readily provided with a radioisotope, for instance shortly before application of the resulting radiolabelled hydroxamate derivative, which is obtained after deprotection and condensation. Deprotection is for instance performed with formic acid or trifluoroacetic acid and condensation can for instance be carried out with hydroxylamine.

It is also possible to react protected valine with the arylsulphonyl or arylphosphonyl halides of formula (II) and subsequently introduce the picolyl group by reacting the product for instance with 3-picolyl chloride.

The hydroxamate group can be exchanged for a phosphate group, such as a monophosphate, a diphosphate or a triphosphate, e.g. by hydrolysis and substitution.

In order to provide the resulting compounds with the one or more desired radioisotopes they can further be reacted to afford one of the following compounds.

In one aspect, the intermediate compound described above (with hydroxamate or phosphate group) can be stannylated or silylated to afford a compound according to formula (I), wherein
Y represents O, $CH_2$, $(CH_2)_2$, S, or NH;
X represents 1-5 substituents,
    wherein said substituents can be the same or different and wherein at least one of said substituents comprises a trialkyltin derivative, preferably Sn(n-butyl)$_3$, or a trialkylsilyl derivative; and
Z is S;
Q is chosen from the group consisting of 3-pyridyl and carboxyl; and
R is chosen from the group consisting of C(=O)—NH—OH,

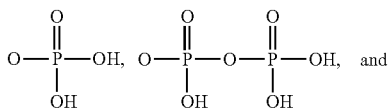

-continued

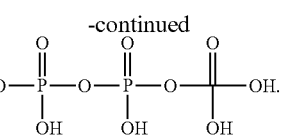

These stannylated or silylated compounds can be subjected to electrophilic radioiodination or radiobromination in order to introduce the radioisotope and obtain the radiolabelled hydroxamate of the invention according to standard methodology (Eersels et al., 2005; Welch et al., 2003; Shiba et al., 2006). The stannylated compounds including alkylated species of Si, Hg, and Ge, can in principle also directly provide access to the $^{18}$F-labelled compounds via electrophilic radiofluorination with $[^{18}F]F_2$ or other $^{18}F$ labelled electrophilic fluorination agents.

In another aspect, intermediate compounds of formula (I), wherein
Y represents O, $CH_2$, $(CH_2)_2$, S, or NH;
X represents 1-5 substituents,
    wherein said substituents can be the same or different and wherein at least one of said substituents comprises Br, I, $N_3$, $NO_2$ or R—$SO_3$, wherein R is an optionally substituted $C_{1-5}$ alkyl group or an optionally substituted phenyl group; and
Z is S;
Q is chosen from the group consisting of 3-pyridyl and carboxyl; and
R is chosen from the group consisting of C(=O)—NH—OH,

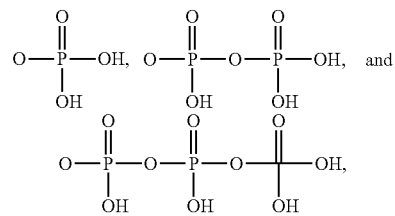

may directly be subjected to nucleophilic aromatic radioiodination or radiobromination in order to introduce the radioisotope and obtain the radiolabelled MMP selective compounds of the invention employing procedures well-known to those skilled in the art (Eersels et al., 2005).

In a particularly preferred embodiment, Cut-assisted nucleophilic aromatic radioiodination, is performed wherein X is Br, Z is S, Q an carbonyl and R is C(=O)—NH—OH.

In yet another aspect, intermediate compounds of formula (I),
wherein Y represents O, $CH_2$, $(CH_2)_2$, S, or NH;
X represents 1-5 substituents,
    wherein said substituents can be the same or different, and wherein at least one of said substituents is a leaving group, preferably selected from $NO_2$, $[N(alkyl)_3]^+$, OTosyl, $N_3$, F, Br, and I, and wherein at least another one of said substituents is an activating group, preferably selected from CHO, $NO_2$, $SO_2CH_3$, $[N(alkyl)_3]^+$, $CF_3$, CN, CO-alkyl, CO-aryl, COOH, Br, Cl, and I; and
Z is S;
Q is chosen from the group consisting of 3-pyridyl and carboxyl; and
R is chosen from the group consisting of C(=O)—NH—OH,

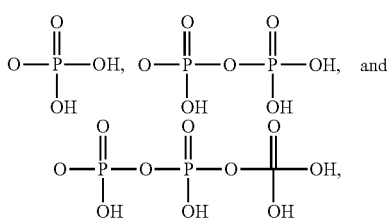

may directly be subjected to nucleophilic aromatic radiohalogenation, in particular nucleophilic aromatic radiofluorination, in order to introduce the radioisotope and obtain the radiolabelled MMP selective compound of the invention employing procedures well-known to those skilled in the art (Al Jammaz et al., 2006; Dolle et al., 1999; Klok et al., 2006; Lemaire et al., 1990, Welch et al., 2003). The activating group is preferably positioned in ortho position with respect to the leaving group, but may for instance also be positioned meta with respect to the leaving group.

Efficient nucleophilic aromatic substitution requires an electron-deficient aromatic system and a suitable leaving group. Typically, nucleophilic fluorination is carried out by heating (or microwave-irradiating) the compound above with $^{18}$F-fluoride complexed with a phase transfer catalyst such as (nBu)$_4$NHCO$_3$ or Kryptofix[2.2.2] in combination with KHCO$_3$ or K$_2$CO$_3$ in a suitable organic solvent, e.g. acetonitrile, dimethyl sulphoxide, dimethyl formamide, sulpholan, dioxane, toluene, or lutidine. Following radiofluorination, the $^{18}$F-labelled product may be decarbonylated by refluxing with an excess of Wilkinson's catalyst (RhCl(Ph$_3$P)$_3$) in toluene (WO-A-2005/037737; Ohno et al., 1968) to yield the $^{18}$F-labelled target compounds.

The radiolabelled MMP selective compounds of the invention can be used to deliver a label to a matrix metalloproteinase (MMP). Advantageously, the MMP selective compounds of the invention are very selective for MMP2 and/or MMP9. Such a label can for instance be provided by using a method comprising contacting a sample comprising said MMP with a radiolabelled MMP selective compound according to the invention.

The invention is also directed to the complex formed between the radiolabelled MMP selective compound according to the invention and a MMP, preferably MMP2 or MMP9.

In a further aspect the radiolabelled MMP selective compounds of the invention can be used to deliver a label to a MMP expressing cell, preferably a MMP2 and/or MMP9 expressing cell. Such a label can for instance be provided by using a method comprising contacting a MMP expressing cell with a radiolabelled MMP selective compound according to the invention.

The radiolabelled MMP selective compounds according to the invention can further be used to quantify MMP on a MMP expressing cell, by contacting the cell with a hydroxamate compound of the invention and determining the amount of bound compound.

The invention further provides in a method for in vivo detection of unstable coronary plaques comprising visualising potential plaques with single-photon emission computed tomography (SPECT) and/or positron emission tomography (PET) using a radiolabelled MMP selective compound according to the invention as a tracer. It can be preferable to use PET, since this technique has a higher sensitivity and better special resolution than SPECT. On the other hand, with the longer half-life of SPECT-ligands and a possible slow biological process of binding and clearance of the radiopharmaceutical, SPECT may be advantageous. The optimal target-to-non target ratio in the image may be reached beyond the half-life of the PET-tracer. Preferably, PET or SPECT is combined with morphologic imaging such as CT. Nowadays hybrid SPECT/CT and PET/CT cameras are available to perform simultaneous molecular and morphologic imaging. It is expected that PET/MRI will become available in the near future.

The radiolabelled MMP selective compounds of the invention further allow in vivo determination of the effectiveness of a potential medicine against unstable plaques in a subject. Such determination comprises i) visualising potential plaques with single-photon emission computed tomography (SPECT) and/or positron emission tomography (PET) using a radiolabelled hydroxamate derivative according to the invention as a tracer;

ii) administering the potential medicine to the subject; and iii) repeating step i) to determine the effectiveness of the potential medicine. Such a method is highly desired, because it is in general very difficult to determine whether a new medicine is effective selectively against unstable plaques.

The invention further concerns a method for treating a coronary atherosclerotic disease in a subject. Unstable coronary plaques in the subject can be identified as described above. Depending on whether such unstable coronary plaques are present the subject can be administered a medicine capable of treating the unstable coronary plaques. Suitable examples of such medicines include the so-called statins and MMP-inhibitors. Advantageously, this method allows for selective treatment of the unstable plaques, whereas conventional methods involve administration of medicines even in the case where such medication may not be necessary, because unstable plaques are not or hardly present or not affected by the treatment.

EXAMPLES

In the text of the examples, the various products (starting material, intermediates, and end products) are referred to in bold in brackets with reference to Schemes 1-4.

Scheme 1 shows the preparation of non-radioactive analogues (5) of compounds according to formula (I).

Scheme 2 shows the synthesis of 4-substituted benzenesulphonyl chlorides (3).

Scheme 3 shows the radiosynthesis of $^{123/125}$I($^{76}$Br)-labelled compounds according to formula (I) for SPECT by stannylation followed by electrophilic radioiodination (radiobromination).

Scheme 4 shows the radiosynthesis of $^{123}$I labelled compound according to formula (I) for SPECT by an Cu$^+$ assisted nucleophilic aromatic radioiodination starting from the bromine hydroxamate precursor in a one step reaction (6a)

Scheme 5 shows the preparation of 2-nitro-5-phenoxybenzaldehyde (12).

Scheme 6 shows the radiosynthesis of $^{18}$F-labelled compounds according to formula (I) for PET. Based on the content of this application as a whole and common general knowledge the person skilled in the relevant art will be able to synthesise these compounds.

The preparation of compound (12) required for the synthesis of one selected representative of precursors (Scheme 4) is illustrated in Scheme 5 starting from 5-chloro-2-nitrobenzaldehyde (Katrizky et al., 2003). Briefly, the reactivity's of the potential leaving groups chloro- and nitro- were reversed by conversion of the aldehyde to the dimethylacetal (10), which was then reacted with sodium phenoxide to the corresponding diaryl ether (11), and deprotected with concentrated aqueous HCl to provide compound (12) in 73% yield over 3 steps.

Materials and Methods $^1$H and $^{13}$C NMR spectra were recorded on a Bruker AC 300 NMR spectrometer; chemical shifts were recorded in parts per million (ppm). Thin Layer Chromatography (TLC) was performed on Merck DC silica-coated aluminium sheets (Silicagel 60, $F_{254}$). Flash column chromatography was performed on Silicagel 60 from J. T. Baker. Unless states otherwise, all chemicals were used without prior purification.

4-Phenoxy-benzenesulphonyl chloride (3a)

To a solution of diphenyl ether 1a (2.00 g, 11.8 mmol) in dry $CH_2Cl_2$ (30 mL) under an argon atmosphere at 0° C., was added chlorosulphonic acid (0.80 mL, 11.8 mmol). The reaction mixture was stirred for 2 h at 0° C. The solvent was evaporated at room temperature and the residue dried overnight under vacuum to give the corresponding 4-phenoxybenzenesulphonic acid (2a) as pink oil. Compound 2a was used for the next reaction without further work-up.

The sulphonic acid (2a) was dissolved in an excess of thionyl chloride (30 mL), a catalytic amount of DMF (cat) was added, and the resulting mixture was stirred for 6 h at reflux. The solvent was evaporated and the residue dissolved in $Et_{20}$ (40 mL). The ether solution was washed with 5% aqueous NaOH (3×40 mL) and water (6×40 mL), dried over anhydrous $MgSO_4$, filtered, and concentrated in vacuo. After drying in high vacuum overnight, the pure product was obtained as a white solid. Yield 63%: 2.09 g, 7.44 mmol, (light yellow syrup). $^1$H-NMR ($CDCl_3$): δ 7.44 (d, $^3J$=9.1 Hz, 2H, ArH), 7.38 (d, $^3J$=9.1 Hz, 2H, ArH), 7.19 (t, 1H, ArH), 7.12 (d, $^3J$=9.1 Hz, 2H, ArH), 6.98 (d, $^3J$=9.1 Hz, 2H, ArH)

4-(4-Fluoro-phenoxy)-benzenesulphonyl chloride (3b)

To a solution of 4-fluorodiphenyl ether 1b (1.00 g, 5.31 mmol) in dry $CH_2Cl_2$ (30 mL) under an argon atmosphere at 0° C., was added chlorosulphonic acid (0.35 mL, 5.31 mmol). The reaction mixture was stirred for 2 h at 0° C. The solvent was evaporated at room temperature and the residue dried overnight under vacuum to give the corresponding 4-(4-fluorophenoxy)benzenesulphonic acid (2b) as a pale-pink hygroscopic solid.

The sulphonic acid intermediate (2b) was then dissolved in an excess of thionyl chloride, a catalytic amount of DMF (few drops) was added, and the resulting mixture was stirred for 6 h at reflux. The solvent was evaporated and the residue dissolved in $Et_2O$ (40 mL). The ether solution was washed with 5% aqueous NaOH (3×40 mL) and water (6×40 mL), dried over anhydrous $MgSO_4$, filtered, and concentrated in vacuo. After drying in high vacuum overnight, the pure product was obtained as a white solid. Yield: 1.04 g, 3.63 mmol, 72% (white solid). $^1$H-NMR ($CDCl_3$): δ 7.99 (d, $^3J$=9.1 Hz, 2H, ArH), 7.19-7.02 (m, 6H, ArH).

4-(4-Chloro-phenoxy)-benzenesulphonyl chloride (3c)

Compound 3c was prepared following the procedure described for 3b with reagent quantities adapted to the amount of starting material 1c (1.00 g, 4.89 mmol). Yield: 0.56 g, 1.85 mmol, 38% (pale yellow solid). $^1$H-NMR ($CDCl_3$): δ 7.83 (d, $^3J$=9.0 Hz, 2H, ArH), 7.62 (d, $^3J$=9.0 Hz, 2H, ArH), 7.57 (d, $^3J$=9.0 Hz, 2H, ArH), 7.45 (d, $^3J$=9.0 Hz, 2H, ArH).

4-(4-Bromo-phenoxy)-benzenesulphonyl chloride (3d)

Compound 3d was prepared following the procedure described for 3b with reagent quantities adapted to the amount of starting material 1d (2.00 g, 8.04 mmol). Yield: 2.70 g, 7.80 mmol, 97% (white solid). $^1$H-NMR ($CDCl_3$): δ 7.99 (d, $^3J$=9.0 Hz, 2H, ArH), 7.55 (d, $^3J$=9.0 Hz, 2H, ArH), 7.05 (d, $^3J$=9.0 Hz, 2H, ArH), 7.00 (d, $^3J$=9.0 Hz, 2H, ArH).

4-(4-Iodo-phenoxy)-benzenesulfonyl chloride (3e)

Compound 3e was prepared following the procedure described for 3b with reagent quantities adapted to the amount of starting material 1e (1.12 g, 3.78 mmol). Yield: 1.20 g, 3.03 mmol, 80% (light pink solid). $^1$H-NMR ($CDCl_3$): δ 8.01 (d, $^3J$=9.0 Hz, 2Hd, ArH), 7.80 (d, $^3J$=8.8 Hz, 2H, ArH), 7.21 (d, $^3J$=9.0 Hz, 2H, ArH), 6.90 (d, $^3J$=9.0 Hz, 2H, ArH).

{[4-Phenoxy-benzenesulphonyl]-tert-butoxycarbonylmethyl-amino}-aceticacid tert-butyl ester (4a)

To a solution of di-O-tBu-protected IDA (1.64 g, 6.67 mmol) in $CH_2Cl_2$ (5 mL) was added triethylamine (0.67 g, 6.67 mmol), followed by a solution 4-phenoxy-benzenesulphonyl chloride (3a) (2.00 g, 7.44 mmol) in $CH_2Cl_2$ (3 mL). After stirring at room temperature overnight, the white solid was filtered off, and the filtrate was evaporated. To the resulting residue was added $H_2O$ (15 mL) and the suspension was extracted with EtOAc (4×40 mL). The combined organic extracts were washed with brine (2×20 mL), dried over anhydrous $MgSO_4$, filtered and evaporated in vacuo to give the pure product. Yield: 2.78 g, 5.82 mmol, 78% (light brown oil). $^1$H-NMR (DMSO-d6): δ 7.91 (d, 2H, $^3J_{HH}$=9.0 Hz, ArH), 7.20 (d, 2H, $^3J_{HH}$=9.0 Hz, ArH), 7.25 (d, 2H, $^3J_{HH}$=9.0 Hz, ArH), 6.98 (d, 1H, $^3J_{HH}$=9.0 Hz, ArH), 6.92 (d, 2H, $^3J_{HH}$=9.0 Hz, ArH), 4.00 (s, 4H, 2×$CH_2CO_2$ tBu), 1.39 (s, 18H, 2×$CO_2tBu$).

{[4-(4-Fluoro-phenoxy)-benzenesulphonyl]-tert-butoxycarbonylmethyl-amino}-aceticacid tert-butyl ester (4b)

To a solution of di-O-tBu-protected IDA (0.50 g, 2.04 mmol) in $CH_2Cl_2$ (4 mL) was added triethylamine (0.21 g, 2.04 mmol), followed by a solution of 4-(4-fluoro-phenoxy)-benzenesulphonyl chloride (3b) (0.64 g, 2.24 mmol) in $CH_2Cl_2$ (2 mL). After stirring at room temperature overnight, the organic solvent was evaporated, and to the resulting residue was added $H_2O$ (15 mL). The suspension was extracted with EtOAc (4×40 mL), and the combined organic extracts washed with brine (2×20 mL), dried over anhydrous $MgSO_4$, filtered and evaporated in vacuo to give the pure product. Yield: 1.01 g, 2.03 mmol, 99% (white solid). $^1$H-NMR (DMSO-d6): δ 7.91 (dd, 2H, $^3J_{HH}$=9.0 Hz, $^4J_{HF}$=5.1 Hz, ArH), 7.42 (t, 2H, $^3J_{HH}$=9.0 Hz, $^3J_{HF}$=9.0 Hz, ArH), 4.07 (s, 4H, 2×$CH_2CO_2H$), 1.40 (s, 18H, 2×$CO_2tBu$).

{[4-(4-Bromophenoxy)-benzenesulphonyl]-tert-butoxycarbonylmethyl-amino}-aceticacid tert-butyl ester (4d)

Compound 4d was prepared similar to the procedure described for 4a using 4-(4-bromophenoxy)-benzenesulphonyl chloride (3d) (3.00 g, 8.63 mmol). Yield: 4.13 g, 7.42 mmol, 86% (light yellow solid). $^1$H NMR (DMSO-d6): δ 7.70

(d, J=8.2 Hz, 2H, ArH), 7.52 (d, J=8.8 Hz, 2H, ArH), 7.01 (d, $^3$J=8.8 Hz, 2H, ArH), 6.67 (d, $^3$J=8.9 Hz, 2H, ArH) 4.05 (s, 4H, 2×CH$_2$CO$_2$ tBu), 1.46 (s, 18H, 2×CO$_2$tBu).

{[4-(4-Iodo-phenoxy)-benzenesulphonyl]-tert-butoxycarbonylmethyl-amino}-aceticacid tert-butyl ester (4e)

Compound 4e was prepared following the procedure described for 4a with reagent quantities adapted to the amount of starting material 3e (0.71 g, 1.81 mmol). Yield: 1.04 g, 1.64 mmol, 99% (white solid). $^1$H-NMR (DMSO-d6): δ 7.96 (d, $^3$J=8.5 Hz, 2H, ArH), 7.59 (d, $^3$J=8.5 Hz, 2H, ArH), 4.07 (s, 4H, 2×CH$_2$CO$_2$H), 1.40 (s, 18H, 2×CO$_2$tBu).

{[4-Phenoxy-benzenesulphonyl]-carboxymethyl-amino}-acetic acid (5a)

Compound 4a (1.02 g, 2.14 mmol) was dissolved in formic acid (10 mL) and stirred overnight at room temperature. The solid was filtered off, the filtrate was evaporated in vacuo, and co-evaporated with toluene (6×20 mL). The pure product obtained was dried overnight in high vacuum. Yield: 0.71 g, 1.95 mmol, 91% (off-white solid). $^1$H-NMR (DMSO-d6): δ 7.91 (d, 2H, $^3$J$_{HH}$=9.0 Hz, ArH), 7.20 (d, 2H, $^3$J$_{HH}$=9.0 Hz, ArH), 7.28 (d, 2H, $^3$J$_{HH}$=9.0 Hz, ArH), 7.00 (d, 1H, $^3$J$_{HH}$=9.0 Hz, ArH), 6.87 (d, 2H, $^3$J$_{HH}$=9.0 Hz, ArH), 4.07 (s, 4H, 2×CH$_2$CO$_2$H).

{[4-(4-Fluoro-phenoxy)-benzenesulphonyl]-carboxymethyl-amino}-acetic acid (5b)

{[4-(4-Fluoro-phenoxy)-benzenesulphonyl]-tert-butoxycarbonyl methyl-amino}-acetic acid tert-butyl ester (4b) (1.00 g, 2.03 mmol) was dissolved in formic acid (10 mL) and stirred overnight at room temperature.

The solid was filtered off and the filtrate was evaporated in vacuo and co-evaporated with toluene (6×20 mL). The pure product was obtained as an off-white solid and dried overnight in high vacuum. Yield: 0.68 g, 1.78 mmol, 88% (off-white solid). $^1$H-NMR (DMSO-d6): δ 7.91 (dd, 2H, $^3$J$_{HH}$=9.0 Hz, $^4$J$_{HF}$=5.1 Hz, ArH), 7.42 (t, 2H, $^3$J$_{HH}$=9.0 Hz, $^3$J$_{HF}$=9.0 Hz, ArH), 4.07 (s, 4H, 2×CH$_2$CO$_2$H).

{[4-(4-Bromo-phenoxy)-benzenesulphonyl]-carboxymethyl-amino}-acetic acid (5d)

Compound 5d has successfully been prepared by direct coupling of 4-(4-bromo-phenoxy)-benzenesulphonyl chloride (3d) to unprotected IDA following originally described procedure (Santos et al., 2006). Briefly, to a solution of IDA (0.93 g, 7.02 mmol) and KOH (1.36 g, 24.2 mmol) in water (5 mL) was added a solution of 4-(4-bromophenoxy)benzenesulphonyl chloride (3d) (2.70 g, 7.80 mmol) in THF (25 mL), and the resulting suspension was stirred for 3 days at room temperature. The organic solvent was evaporated, the residue dissolved in 5% aqueous NaOH (40 mL), and the insoluble white solids were filtered off. The aqueous solution was washed with DCM (3×40 mL), acidified to pH 1 with concentrated aqueous HCl, and extracted with EtOAc (6×40 mL). The combined EtOAc-layers were dried over anhydrous MgSO$_4$, filtered and evaporated in vacuo to give the pure product. Yield: 1.90 g, 4.30 mmol, 61% (white solid). $^1$H-NMR (DMSO-d6): δ 7.82 (d, J=8.8 Hz, 2H, ArH), 7.64 (d, J=8.8 Hz, 2H, ArH), 7.17-7.07 (m, 4H, ArH), 3.96 (s, 4H, 2×CH$_2$CO$_2$H).

{[4-(4-Iodo-phenoxy)-benzenesulphonyl]-carboxymethyl-amino}-acetic acid (5e)

Compound 5e was prepared following the procedure described for 5b with reagent quantities adapted to the amount of starting material 5d (0.68 g, 1.08 mmol). Yield: 0.50 g, 1.02 mmol, 94% (white solid). $^1$H-NMR (DMSO-d6): δ 7.82 (d, J=8.8 Hz, 2H, ArH), 7.64 (d, J=8.8 Hz, 2H, ArH), 7.17-7.07 (m, 4H, ArH), 3.96 (s, 4H, 2×CH$_2$CO$_2$H).

{[4-Phenoxy-benzenesulphonyl]-hydroxycarbamoyl-methyl-amino}-acetic acid (6a)

Compound 5a (711 mg, 1.95 mmol) was dissolved in dry THF (5 mL). ECF (160 µL, 1.95 mmol), and NMM (180 µL, 1.95 mmol) were added and this mixture was stirred for 40 min at 0° C. NH$_2$OH.HCl (136 mg, 1.95 mmol) and KOH (109 mg, 1.95 mmol) were dissolved in dry MeOH (5 mL) and stirred at 0° C. for 30 min. The solids were filtered off, and the THF solution was added dropwise to the methanol filtrate and stirred for 2 h at 0° C. The reaction mixture was filtered, the solvent evaporated, and the residue dissolved in H$_2$O (25 mL). After adjusting the pH to 1-2, the aqueous layer was extracted with EtOAc (3×30 mL). The combined organic layers were dried over MgSO$_4$, evaporated in vacuo, and co-evaporated with EtOAc (3×3 mL) to yield the pure product as light-pink solid. Yield: 565 mg, 1.10 mmol, 56%. $^1$H-NMR (DMSO-d6): δ 7.87 (d, 2H, $^2$J$_{HH}$=9.0 Hz, ArH), 7.42 (d, 2H, $^2$J$_{HH}$=9.0 Hz, ArH), 7.35 (s, 2H, ArH), 6.98 (d, 1H, $^3$J$_{HH}$=9.0 Hz, ArH), 6.90 (d, 2H, $^3$J$_{HH}$=9.0 Hz, ArH), 4.07 (s, 2H, 2×CH$_2$CO$_2$H), 3.85 (s, 2H, 2×CH$_2$CONHOH). ESI-MS calcd for C$_{16}$H$_{16}$N$_2$O$_7$S 380.07 [M-H]$^-$, obsd 381.1.

{[4-(4-Fluoro-phenoxy)-benzenesulphonyl]-hydroxycarbamoylmethyl-amino}-acetic acid (6b)

{Carboxymethyl-[4-(4-bromo-phenoxy)-benzenesulphonyl]-amino}-acetic acid (4b) (500 mg, 1.30 mmol) was dissolved in dry THF (10 mL). ECF (100 µL, 1.12 mmol), and NMM (120 µL, 1.12 mmol) were added and stirred for 40 min at 0° C. NH$_2$OH×HCl (90 mg, 1.30 mmol) and KOH (73 mg, 1.30 mmol) were dissolved in dry MeOH (10 mL) and stirred at 0° C. for 30 min. The solids were filtered off, and the THF solution was added dropwise to the methanol filtrate and stirred for 2 h at 0° C. The reaction mixture was filtered, the solvent evaporated, and the residue dissolved in H$_2$O (25 mL). After adjusting the pH to 1-2, the aqueous layer was extracted with EtOAc (3×30 mL). The combined organic layers were dried over MgSO$_4$, evaporated in vacuo, and co-evaporated with EtOAc (3×3 mL) to yield the pure product as light-pink solid. Yield: 267 mg, 0.67 mmol, 52%. $^1$H-NMR (DMSO-d6): δ 7.91 (dd, 2H, $^3$J$_{HH}$=9.0 Hz, $^4$J$_{HF}$=5.1 Hz, ArH), 7.42 (t, 2H, $^3$J$_{HH}$=9.0 Hz, $^3$J$_{HF}$=9.0 Hz, ArH), 4.07 (s, 4H, 2×CH$_2$CO$_2$H). ESI-MS calcd for C$_{16}$H$_{15}$FN$_2$O$_7$S 398.06 [M-H]$^-$, obsd 399.10

{[4-(4-Bromo-phenoxy)-benzenesulphonyl]-hydroxycarbamoylmethyl-amino}-acetic acid (6d)

{Carboxymethyl-[4-(4-bromo-phenoxy)-benzenesulphonyl]-amino}-acetic acid (4d) (1.90 g, 4.30 mmol) was dissolved in dry THF (50 mL). ECF (0.35 mL, 3.70 mmol), and NMM (0.40 mL, 3.70 mmol) were added and stirred for 40 min at 0° C. NH$_2$OH×HCl (0.30 g, 4.30 mmol) and KOH (0.24 g, 4.30 mmol) were dissolved in dry MeOH (20 mL) and stirred at 0° C. for 30 min. The solids were filtered off, and the THF solution was added dropwise to the methanol filtrate and stirred for 2 h at 0° C. The reaction mixture was filtered, the solvent evaporated, and the residue dissolved in $H_2O$ (20 mL). After adjusting the pH to 1-2, the aqueous layer was extracted with EtOAc (3×30 mL). The combined organic layers were dried over $MgSO_4$ and evaporated in vacuo to yield the pure product as white crystals. Yield: 1.80 g, 3.90 mmol, 91%. $^1$H NMR ($D_2O$): δ 7.7 (d, J=8.2 Hz, 2H, ArH), 7.5 (d, J=8.8 Hz, 2H, ArH), 7.0 (d, J=8.8 Hz, 2H, ArH), 4.0 (s, 4H, $CH_2COOH$). ESI-MS calcd for $C_{16}H_{15}BrN_2O_7S$ 457.98 [M-H]$^-$, obsd 459.27.

{[4-(4-Iodo-phenoxy)-benzenesulphonyl]-hydroxycarbamoylmethyl-amino}-acetic acid (6e)

Compound 6e was prepared following the procedure described for 6b with reagent quantities adapted to the amount of starting material 5e (500 mg, 1.02 mmol). Yield: 305 mg, 0.60 mmol, 59%. $^1$H NMR ($D_2O$): δ 7.72 (d, $^3$J=8.2 Hz, 2H, ArH), 7.52 (d, $^3$J=8.8 Hz, 2H, ArH), 7.03 (d, $^3$J=8.8 Hz, 2H, ArH), 4.01 (s, 4H, $CH_2COOH$). ESI-MS calcd for $C_{16}H_{15}IN_2O_7S$ 505.97 [M-H]$^-$, obsd 507.0.

{[4-(4-tributylstannyl-phenoxy)-benzenesulphonyl]-tert-butoxycarbonylmethyl-amino}-acetic acid tert-butyl ester (7) (Shiba et al., 2006)

A stirred solution of hexabutylditin (230 mg, 0.40 mmol), {[4-(4-iodo-phenoxy)-benzenesulphonyl]-tert-butoxycarbonylmethyl-amino}-acetic acid tert-butyl ester (4e) (100 mg, 0.16 mmol) and $Pd(PPh_3)_4$ (11 mg, 9 mmol) in toluene (4 mL) was degassed by bubbling argon through the solution for 2 h. The reaction mixture was refluxed overnight under argon atmosphere. The solvent was removed by evaporation and the residue was purified by flash column chromatography (eluent: hexane/EtOAc 4/1) The pure product was obtained as a colourless oil. Yield: 80 mg, 0.10 mmol, 65%. $^1$H-NMR (DMSO-d6): δ 7.89 (s, 2H, ArH), 7.28 (d, $^3$J=8.5 Hz, 2H, ArH), 6.90 (s, 2H, ArH) 4.10 (s, 4H, 2×$CH_2CO_2H$), 1.40 (s, 18H, 2×$CO_2$tBu), 1.33 (s, 12H, 2×{Sn—($CH_2$)$_3$}), 1.01 (s, 6H, 2×Sn—$CH_3$).

{[4-(4-[$^{123}$I]Iodophenoxy)-benzenesulphonyl]-hydroxycarbamoylmethyl-amino}-acetic acid ([$^{123}$I]8) (Method 1)

To a solution of 7 (110 µg, 0.14 mmol) in acetic acid (300 µL) was added Na[$^{123}$I]I (2.4 GBq) in a 0.1 M NaOH solution (ca. 10 µL), followed by addition of 30% $H_2O_2$ (70 µL). The reaction mixture was mixed using a Vortex-apparatus, left at room temperature for 15 min and subsequently quenched with a saturated solution of sodium bisulphite (0.1 mL), and followed by addition of saturated sodium bicarbonate solution (0.2 mL). The reaction mixture was loaded onto a Sep-Pak® $C_{18}$-cartridge (preconditioned with 5 mL of EtOH followed by 10 mL of $H_2O$). The $C_{18}$-cartridge was washed with water (3×10 mL) and dried under a continuous flow of $N_2$. Removal of the t-butyl protecting groups was performed by eluting the $C_{18}$ cartridge with 2 M HCl in $Et_2O$ (0.5 mL) and reaction at room temperature for 30 min. After this period the $Et_2O$ was evaporated under a continuous flow of argon. Dry THF, NMM, and ECF (500 µL, 250 µL, 250 µL) was added and the reaction mixture was cooled to 0° C. and left at this temperature for 5 min. The THF-solution was added dropwise to a freshly prepared solution of $NH_2OH$ in MeOH and left for 15 min at 0° C. Of this reaction mixture 2 mL was loaded onto a Sep-Pak® $C_{18}$-cartridge and washed (3×10 mL $H_2O$). The Sep-Pak® was eluted with EtOH (500 µL) and this ethanol solution, containing the product [$^{123}$I]8, was subjected to HPLC purification Chromasil C-18 column with 25% ACN/0.08 M Phosphate buffer in $H_2O$ as eluent at a flow of 5 mL/min.

{[4-(4-[$^{123}$I]Iodophenoxy)-benzenesulphonyl]-hydroxycarbamoylmethyl-amino}-acetic acid ([$^{123}$I]8) (Method 2)

Compound 6d (1.6 mg, 3.7 mmol) was dissolved in an solution of ethanol and water (350 µL/150 µL) respectively, followed by addition of gentisic acid (5.5 mg, 35.6 mmol), citric acid (4.2 mg, 21.9 mmol) and a catalytic amount of $SnSO_4$. The mixture was vigorously stirred for 30 s. 35 µL of a 3.3 M solution of $CuSO_4$ (100 mmol) was added to the reaction mixture followed by the addition of Na[$^{123}$I]I (2.0 GBq) in a 0.1 M NaOH solution. The reaction mixture was put under dry nitrogen for 15 min and heated to 140° C. for 40 min. After cooling to room temperature, 500 µL of an $H_2O$/ethanol (8/2) mixture was added to the reaction mixture and filtered over a 0.5 µM Millex® LCR3PTE filter. The filtrate, containing the product [$^{123}$I]8, was purified on HPLC using an Chromasil C-18 column with 25% ACN/0.08 M phosphate buffer in $H_2O$ as eluent at a flow of 3.5 mL/min.

Preliminary in vitro inhibition studies revealed that the compounds potently inhibited MMPs with excellent selectivity for MMP-2 and MMP-9, supporting that radiolabelled tracers based on the structure of these inhibitors can enable imaging of unstable plaques in vivo.

TABLE 1

Preliminary results for the synthesis and MMP inhibitory potencies of N-haloaryl-substituted hydroxamates derivatives.

| MMP inhibitors of general structure (1) | X | Y | Yield (%) | $IC_{50}$ MMP-1 [µm] | MMP-2 [nm] | MMP-9 [nm] |
|---|---|---|---|---|---|---|
| 6a | H | O | 71 | 1.67 ± 0.98 | 1.89 ± 1.11 | 4.31 ± 2.06 |
| 6b | F | O | 58 | 4.69 ± 2.22 | 0.13 ± 0.03 | 0.27 ± 0.15 |
| 6d | Br | O | 73 | 0.91 ± 0.56 | 0.87 ± 0.40 | 1.95 ± 1.10 |
| 6e | I | O | 39 | 1.32 ± 0.79 | 7.64 ± 1.43 | 1.61 ± 1.41 |

Figure 1:
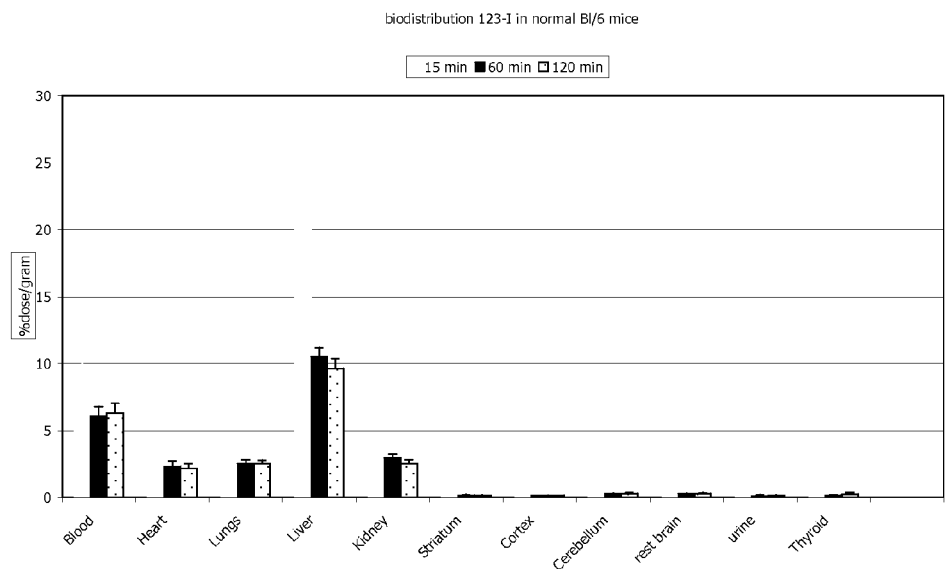

Because the in vitro studies gave promising results, preliminary in vivo studies were performed using the CL57/BL6 mice (8 weeks old). The tissue distribution of [$^{123}$I]8 (which is representative for the radioisotopes with alternative halogens), after intravenous administration, was determined at three time points. The results of a normal biodistribution studies are shown in FIG. 1. The results show that [$^{123}$I]8 is taken up intensively into the liver and is excreted mainly via the urinary tract. This is regular pharmacokinetic behaviour of a radiotracer. Only a very low uptake in the thyroid was observed, giving evidence for a low de-iodination in vivo, an important prerequisite for radio-iodinated radiopharmaceuticals.

Figure 2:
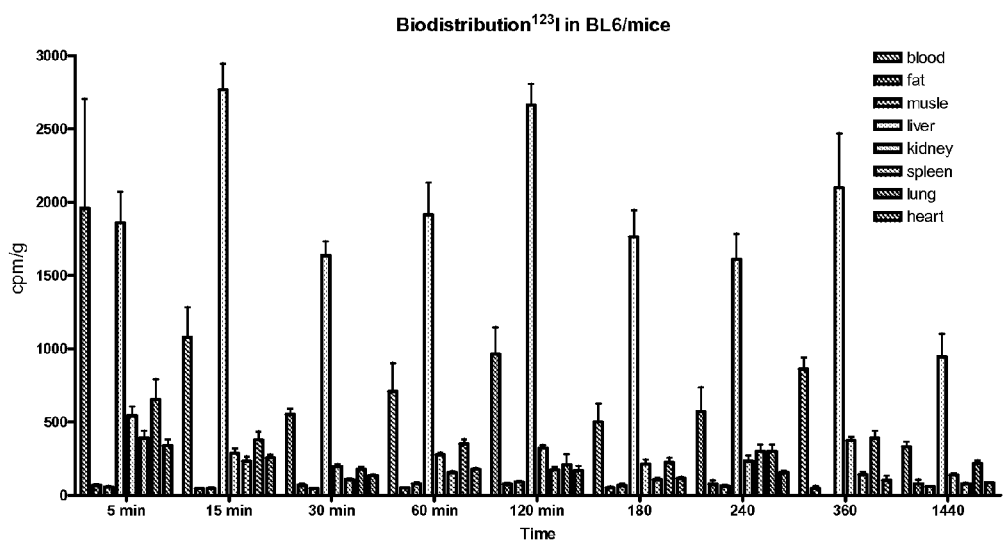

The extended biodistribution studies were performed using the CL57/BL6 mice (8 weeks old). Here the tissue distribution of [$^{123}$I]8, after intravenous administration was determined at 9 time points (up to 24 hours p.i.). A little re-uptake was observed in the liver and kidney after 3 and 6 hours respectively, which is probably related to the formation of metabolites (FIG. 2).

Apolipoprotein deficient pro-atherogenic mice (ApoE−/−; Charles River Laboratories, cat. nr. B6.129P2-ApoE$^{tm1Unc}$/Crl) develop atherosclerotic plaques spontaneously in large arterial blood vessels. The most prominent plaques are observed in the aortic sinus area, at the site of the aortic valves in the heart. Four month old ApoE−/− mice were given a Western Type diet (cat nr. 4021.06; Arie Blok Diervoeding, Woerden, the Netherlands), during one month to stimulate atherogenesis. On the last day of the experiment the radiolabeled MMP-2 antagonist was given by intravenous injection. Three hours after injection, the mice were harvested and the aortic sinus area was analysed overnight using a storage phosphor imaging technique for binding of the MMP2 antagonist.

Increased radioactivity was observed in the aortic sinus of the heart (FIG. 3 A, C; arrow 1 indicates corresponding plaques). The elevated lipid levels in the blood, due to ApoE deficiency and the Western Type diet, lead to increased atherosclerotic plaque formation in the aortic root as demonstrated by Oil-red-O immunohistochemical neutral lipid staining (cat nr. O-0625; Sigma-Aldrich, the Netherlands) (FIG. 3 B, D; arrow 2 indicates corresponding plaques). Comparison of the radiolabeled image of the aortic root with the Oil-red-O staining showed increased radioactivity in proximity of the atherosclerotic plaques that are stained red where lipid-rich macrophages are present. The advanced atherosclerotic plaques are a known source of MMP-2 and co-localisation of the increased radioactivity and the plaque area reveals the potential of the MMP-2 antagonist to visualise the atherosclerotic plaques in vivo.

REFERENCES

Al Jammaz, I.; Al-Otaibi, B.; Okarvi, S.; and Amartey, J. *Journal of Labelled Compounds & Radiopharmaceuticals* 2006, 49, 125-137.

Cai, L.; Lu, S.; Pike, V. W. *Eur. J. Org. Chem.* 2008, 2853-2873.

Choi, S. H.; Chae, A.; Chen, C. H.; Merki, E.; Shaw, P. X.; and Tsimikas, S. *Current Opinion in Biotechnology* 2007, 18, 73-82.

Davies, J. R.; Rudd, J. H.; Weissberg, P. L.; and Narula, J. *Journal of the American College of Cardiology* 2006, 47, C57-68.

Davies, J. R.; Rudd, J. H. F.; Fryer, T. D.; Graves, M. J., Clark, J. C.; Kirkpatrick, P. J.; Gillard, J. H.; Warburton, E. A.; and Weissberg, P. L. *Stroke* 2005, 36, 2642-2647.

Dolle, F.; Dolci, L.; Valette, H.; Hinnen, F.; Vaufrey, F.; Guenther, I.; Fuseau, C.; Coulon, C.; Bottlaender, M.; and Crouzel, C. *Journal of Medicinal Chemistry* 1999, 42, 2251-2259.

Eersels, J. L. H.; Travis, M. J.; and Herscheid, J. D. M. *Journal of Labelled Compounds & Radiopharmaceuticals* 2005, 48, 241-257.

Hu, J. L.; Van den Steen, P. E.; Sang, Q. X. A.; and Opdenakker, G. *Nature Reviews Drug Discovery* 2007, 6, 480-498.

Katritzky, A. R.; Wang, Z. Q.; Hall, C. D.; and Akhmedov, N. G. *Arkivoc* 2003, 49-58.

Klok, R. P.; Klein, P. J.; Herscheid, J. D. M.; and Windhorst, A. D. *Journal of Labelled Compounds & Radiopharmaceuticals* 2006, 49, 77-89.

Lemaire, C.; Guillaume, M.; Cantineau, R.; and Christiaens, L. *Journal of Nuclear Medicine* 1990, 31, 1247-1251.

Ogawa M.; Magata Y.; Kato, T.; Hatano, K.; Ishino, S.; Mukai, T.; Shiomi, M.; Ito, K.; and Saji, H. *Journal of Nuclear Medicine* 2006, 47, 1845-1850.

Ohno, K.; and Tsuji, J. *Journal of American Chemical Society* 1968, 90, 99-107.

Ranganna, K.; Yatsu, F. M.; and Mathew O. P. *Vascular Disease Prevention* 2006, 3, 375.

Rouis, M. *Current Drug Targets—Cardiovascular & Haematological Disorders* 2005, 5, 541-548.

Rudd, J. H. F.; Warburton, E. A.; Fryer, T. D., Jones, H. A.; Clark, J. C.; Antoun, N.; Johnstrom, P.; Davenport, A. P.; Kirkpatrick, P. J.; Arch. B. N. *Circulation* 2002, 105, 2708-2711.

Santos, M. A.; Marques, S. M.; Tuccinardi, T.; Carelli, P.; Panelli, L.; and Rossello, A. *Bioorganic & Medicinal Chemistry* 2006, 14, 7539-7550.

Schäfers, M.; Riemann, B.; Kopka, K.; Breyholz, H. J.; Wagner, S.; Schäfers, K. P.; Law, M. P.; Schober, O.; and Levkau, B. *Circulation* 2004, 109, 2554-2559.

Shiba, K.; Ogawa, K.; Ishiwata, K.; Yajima, K.; and Mori, H. *Bioorganic and Medicinal Chemistry* 2006, 14, 2620-2626.

Schubiger, P. A.; Lehman, L.; Friebe, M. eds. "PET Chemistry, the driving force in molecular imaging" Springer, 2006, Chapters 2, 3, 4 and 5.

Skiles, J. W.; Gonnella, N. C.; and Jeng, A. Y. *Current Medicinal Chemistry* 2001, 8, 425-474.

Skiles, J. W.; Gonnella, N. C.; and Jeng. A. Y. *Current Medicinal Chemistry* 2004, 11, 2911-2977.

Tahara, N.; Kai, H.; Ishibashi, M.; Nakaura, H.; Kaida, H.; Baba, K.; Hayabuchi, N.; and Imaizumi, T. *Journal of the American College of Cardiology* 2006, 48, 1825-1831.

Tawakol, A.; Migrino, R. Q.; Bashian, G. G.; Bedri, S.; Vermylen, D.; Cury, R. C.; Yates, D.; LaMuraglia, G. M.; Furie, K.; Houser, S.; Gewirtz, H.; Muller, J. E.; Brady, T. J.; and Fischman A. J. *Journal of the American College of Cardiology* 2006, 48, 1818-1824.

Vallabhajosula, S.; and Fuster, V. *Journal of Nuclear Medicine* 1997, 38, 1788-1796.

Wagner, S.; Breyholz, H. J.; Faust, A.; Holtke, C.; Levkau, B.; Schober, O.; Schäfers, M.; and Kopka, K. *Current Medicinal Chemistry* 2006, 13, 2819-2838.

Wagner, S.; Breyholz, H. J.; Law, M. P.; Faust, A.; Holtke, C.; Schroer, S.; Haufe, G.; Levkau, B.; Schober, O.; Schäfers, M.; and Kopka, K. *Journal of Medicinal Chemistry* 2007, 50, 5752-5764.

Wester, H. J. in "Handbook of Nuclear Chemistry, Volume 4", ed. Vértes, A.; Nagy, S.; Klencsár, Z., Kluwer Academic Publishers, 2003, Amsterdam, 167-209.

Welch, M. J.; and Redvanly, C. S. "Handbook of Radiopharmaceuticals", 2003, Chicester: John Wiley & Sons.

Yun, M. J.; Yeh, D.; Araujo, L. I.; Jang, S. Y.; Newberg, A.; and Alavi, A. *Clinical Nuclear Medicine* 2001, 26, 314-319.

Schemes

Scheme 1

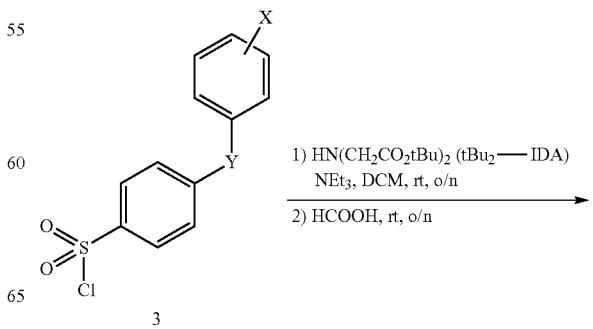

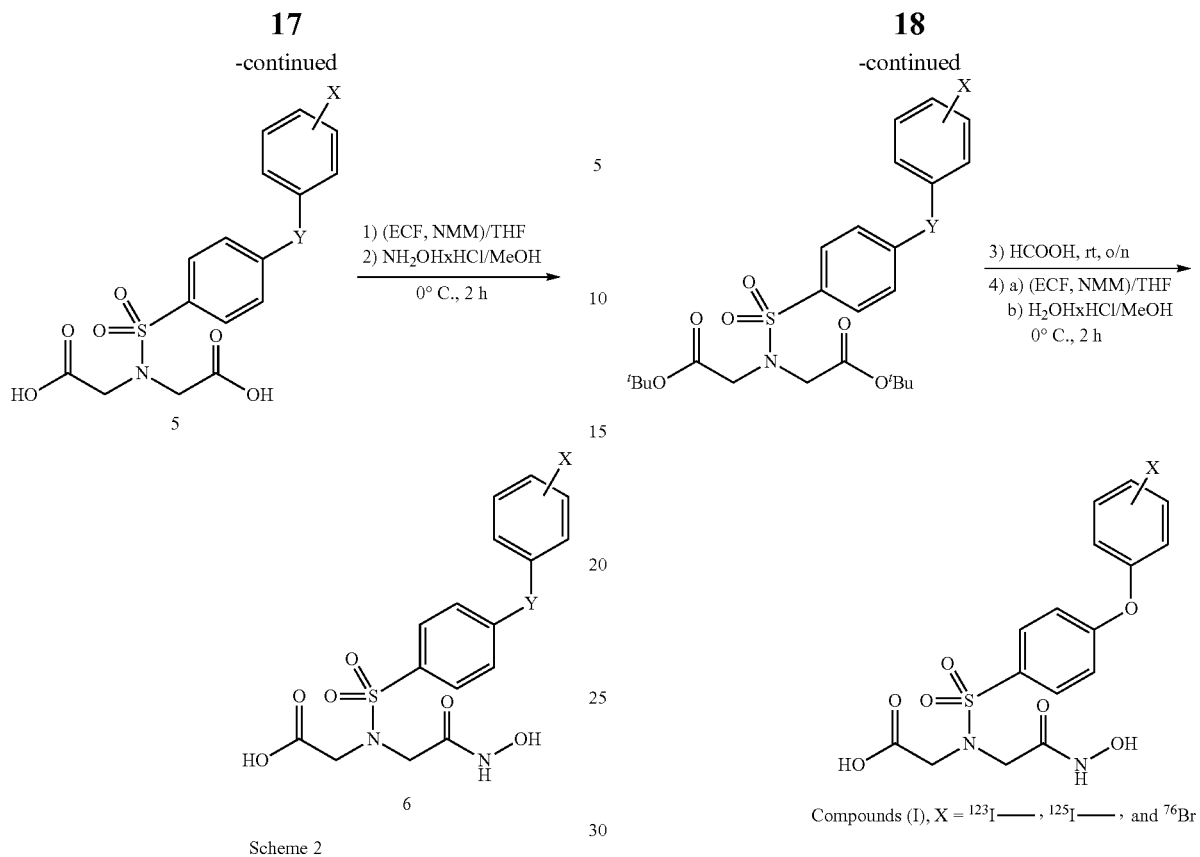
Scheme 2
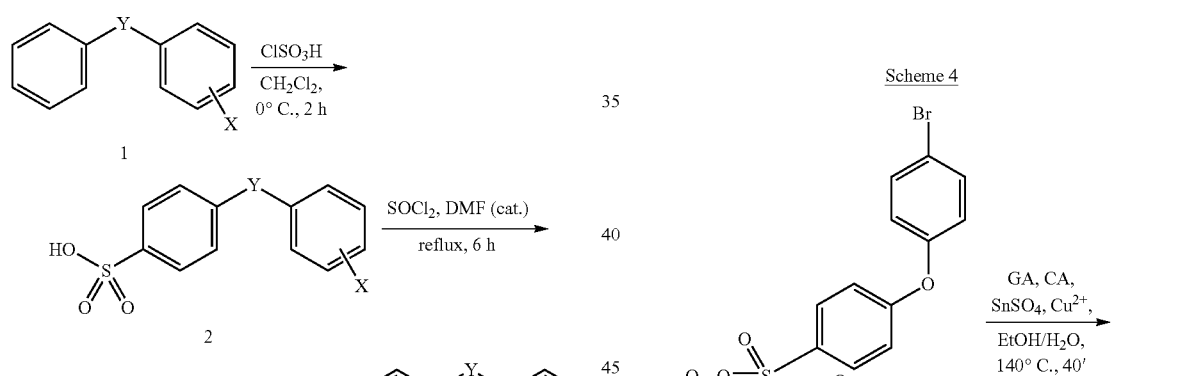
Scheme 3
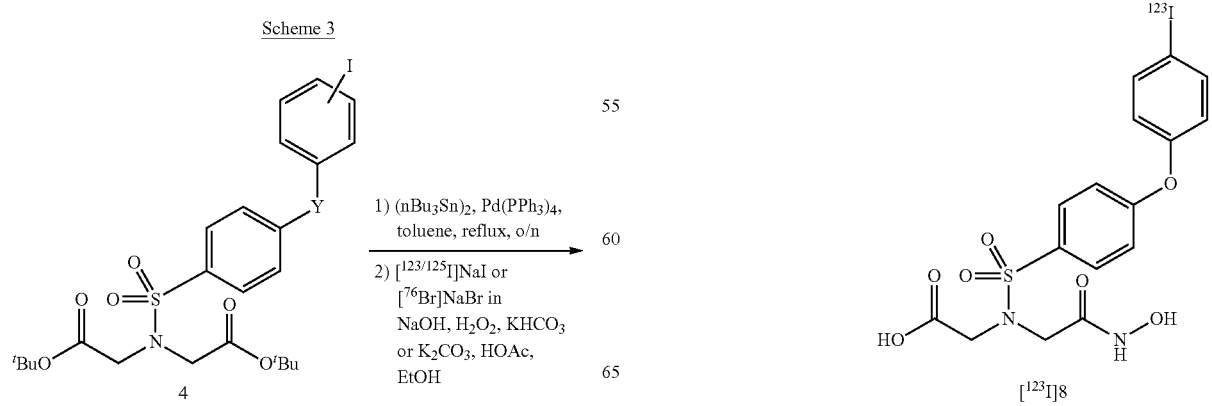

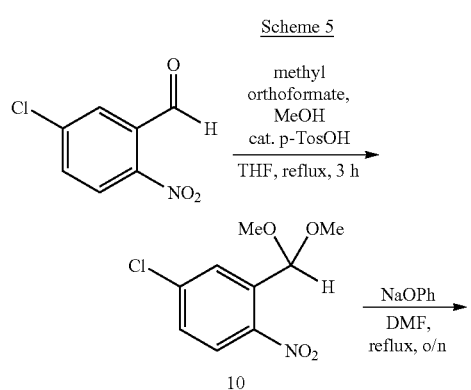
Scheme 5
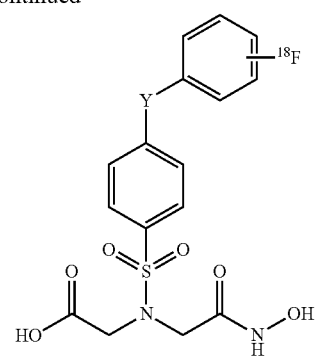
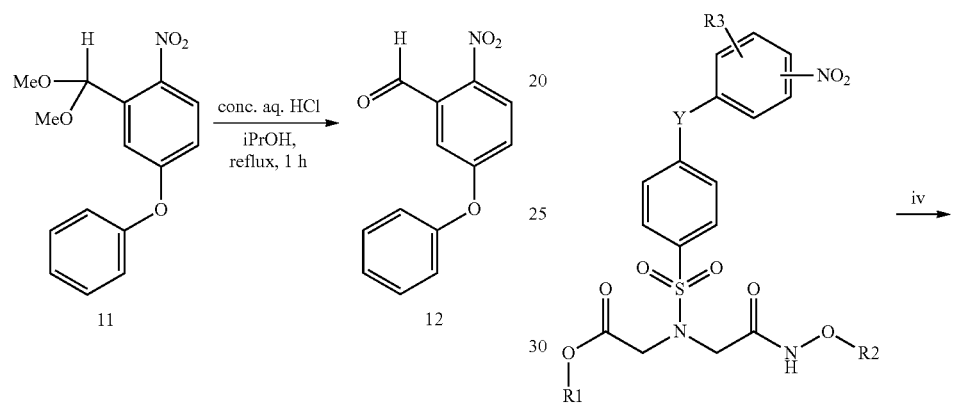
Scheme 6
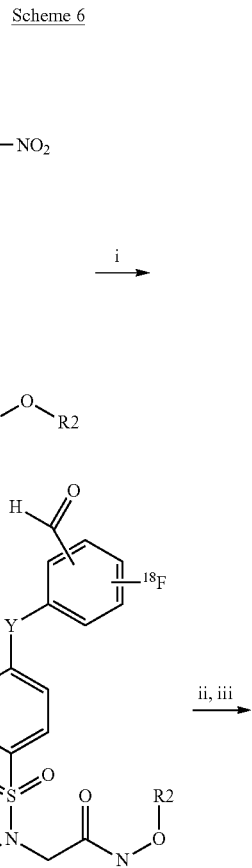
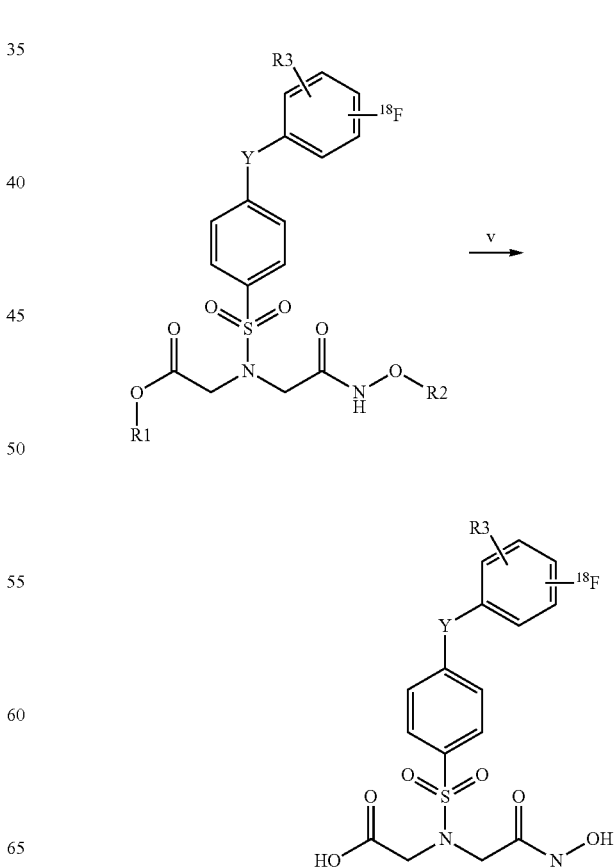

-continued

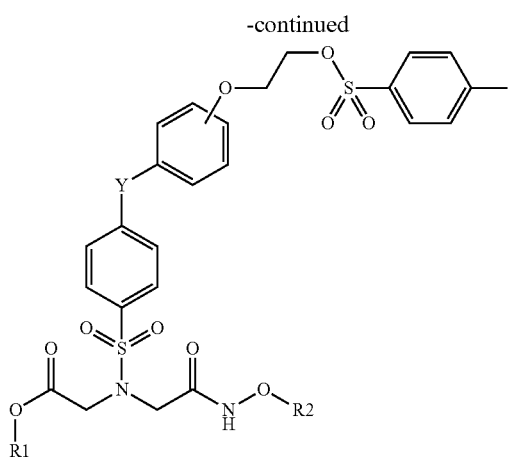

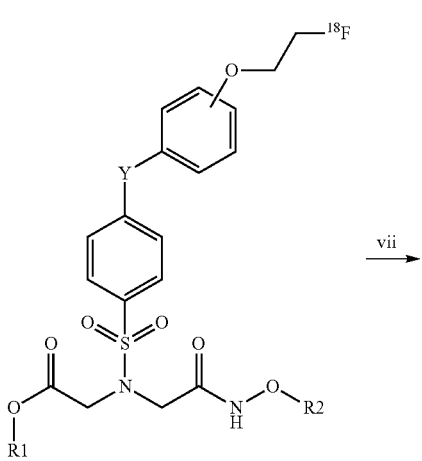

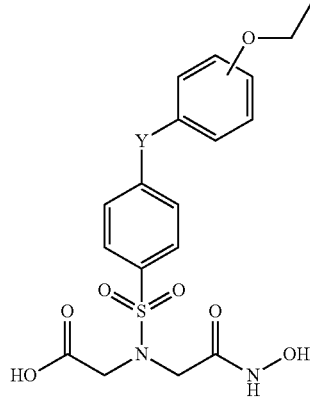

Reaction conditions.
i: K[$^{18}$F]F—K$_{222}$, K$_2$CO$_3$, heating (80-150° C.), 1-30 min, DMSO; ii: RhCl(Ph$_3$)$_3$ (excess), toluene, reflux, 15-120 min; iii: H$^+$, heating (50-100° C.), 5-15 min, DMSO/H$_2$O; iv K[$^{18}$F]F—K$_{222}$, K$_2$CO$_3$, heating (80-150° C.), 1-30 min, DMSO; v: H$^+$, heating (50-100° C.), 5-15 min, DMSO/H$_2$O; vi: K[$^{18}$F]F—K$_{222}$, K$_2$CO$_3$, heating (80-150° C.), 1-30 min, DMSO; vii: H$^+$, heating, 5-15 min, DMSO/H$_2$O R1 and R2 represent acid labile protecting groups, such as a t-butyl ester, a t-butyloxycarbamate (BOC-group), or a benzyloxycarbamate (Z-group)
R3 is an electron withdrawing group, positioned para or ortho relative to the nitro leaving group.

The invention claimed is:

1. Compound having the formula (I)

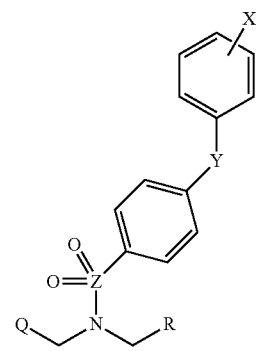

wherein
Y is O, CH$_2$, (CH$_2$)$_2$, S, NH, or C(=O)NH;
X represents 1-5 substituents,
wherein said substituents can be the same or different wherein at least one of said substituents comprises Br, I, N$_3$, NO$_2$, or R—SO$_3$, wherein R is an optionally substituted C1-5 alkyl group or an optionally substituted phenyl group and wherein at least one of said substituents comprises a radioisotope suitable for PET and/or SPECT and/or a β-emitter
Z is S;
Q is selected from the group consisting of 3-pyridyl and carboxyl; and
R is selected from the group consisting of C(=O)—NH—OH,

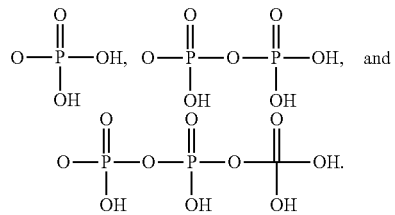

2. Compound according to claim 1, wherein X comprises at least one radioisotope selected from the group consisting of $^{123}$I, $^{124}$I, $^{125}$I, $^{131}$I, $^{76}$Br, $^{18}$F, and $^{11}$C.

3. Compound according to claim 1, wherein X represents one substituent in ortho, meta, or para position.

4. Compound according to claim 1, wherein one or more of said X substituents comprises a linear or branched saturated or unsaturated C$_{1-10}$ alkyl chain.

5. Compound according to claim 1, wherein one or more of said X substituents is selected from halogens, aldehydes, ketones, carboxylates, nitriles, azides, nitro-groups, nitroso-groups, esters, optionally substituted saturated or unsaturated linear or branched alkyl chains, aryls, heteroaryls, saturated or unsaturated linear or branched alkoxys, aryloxys, saturated or unsaturated linear or branched alkylaminos, and arylaminos.

6. Compound according to claim 5, wherein one or more of X substituents is selected from the group consisting of saturated or unsaturated linear or branched alkoxys comprising a halogen radioisotope, aryloxys comprising a halogen radioisotope, saturated or unsaturated alkylaminos comprising a halogen radioisotope, and arylaminos comprising a halogen radioisotope.

7. Compound according to claim 1, wherein said 1-5 X substituents is selected from the group consisting of —O—$C_2H_4$—$^{18}F$, —O—$C_3H_6$—$^{18}F$, —O—$(CH_2)_n$—$C_2H_2$—$^{18}F$, —O—$(CH_2)_n$—$C_2H_2$—$^{123}I$, —NH—$C_2H_4$—$^{18}F$, —NH—$C_3H_6$—$^{18}F$, —NH—$(CH_2)_n$—$C_2H_2$—$^{18}F$, —NH—$(CH_2)_n$—$C_2H_2$—$^{123}I$, wherein n is an integer between 1 and 10.

8. Compound according to claim 1, wherein Y represents O, S or NH.

9. Compound according to claim 1, wherein Q is carboxyl, and R is C(=O)—NH—OH.

10. Compound according to claim 1, wherein
   Y is O, $CH_2$, $(CH_2)_2$, S, or NH;
   wherein said X substituents can be the same or different and wherein at least one of said substituents comprises a trialkyltin derivative, or a trialkylsilyl derivative.

11. Compound according to claim 1, wherein
   Y represents O, $CH_2$, $(CH_2)_2$, S, or NH;
   wherein said substituents can be the same or different,
   and wherein at least one of said substituents is a leaving group,
   and wherein at least another one of said substituents is an activating group.

12. Compound according to claim 11, wherein said activating group is positioned in ortho, position with respect to the leaving group.

13. A method for providing a matrix metalloproteinase (MMP) with a label comprising contacting a sample comprising said MMP with a compound according to claim 1.

14. A complex of a compound according to claim 1 and an MMP.

15. A method for labeling a MMP expressing cell with a label comprising contacting an MMP expressing cell with a compound according to claim 1.

16. A method for quantifying MMP on an MMP expressing cell, comprising contacting said cell with a compound according to claim 1 and determining the amount of bound compound.

17. Method for identifying unstable coronary plaques in a subject comprising administering a compound of claim 1 as a tracer for visualising potential plaques with single-photon emission computed tomography (SPECT) and/or positron emission tomography (PET).

* * * * *

UNITED STATES PATENT AND TRADEMARK OFFICE
CERTIFICATE OF CORRECTION

PATENT NO. : 8,524,194 B2
APPLICATION NO. : 12/992592
DATED : September 3, 2013
INVENTOR(S) : Bertha Louise Frederike Van Eck-Smit et al.

It is certified that error appears in the above-identified patent and that said Letters Patent is hereby corrected as shown below:

On the title page, line (73) the following Assignee information should be inserted underneath Assignee ACADEMISCH MEDISCH CENTRUM BIJ DE UNIVERSITEIT VAN AMSTERDAM:

-- VERENIGING VOOR CHRISTELIJK HOGER ONDERWIJS, WETENSCHAPPELIJK ONDERZOEK EN PATIËNTENZORG
    AMSTERDAM (NL) --

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,524,194 B2
APPLICATION NO.    : 12/992592
DATED              : September 3, 2013
INVENTOR(S)        : Van Eck-Smit et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 362 days.

Signed and Sealed this
Fifteenth Day of September, 2015

Michelle K. Lee
*Director of the United States Patent and Trademark Office*